United States Patent [19]

Owen

[11] Patent Number: 4,836,596
[45] Date of Patent: Jun. 6, 1989

[54] TWEEZERS AND MAGNIFIER

[76] Inventor: Ronald C. Owen, 6614 W. Diversey Ave., Chicago, Ill. 60636

[21] Appl. No.: 275,606

[22] Filed: Nov. 23, 1988

Related U.S. Application Data

[63] Continuation of Ser. No. 38,738, Apr. 15, 1987, abandoned.

[51] Int. Cl.$^4$ .............................................. B25B 9/02
[52] U.S. Cl. .................................. 294/99.2; 128/354
[58] Field of Search ............... 294/99.2; 128/354, 355; D24/23, 27

[56] References Cited

U.S. PATENT DOCUMENTS

| D. 170,945 | 11/1953 | Robitschek . | |
|---|---|---|---|
| D. 230,100 | 1/1979 | Hornbeck . | |
| 718,748 | 1/1903 | Boehm . | |
| 1,765,366 | 6/1930 | Crater . | |
| 2,070,798 | 2/1937 | Mason . | |
| 2,435,791 | 2/1948 | Fleenor | 294/99.2 |
| 4,524,647 | 6/1985 | Holoff | 294/99.2 |

FOREIGN PATENT DOCUMENTS

| 101275 | 6/1921 | Switzerland . |
| D. 982892 | 1/1978 | United Kingdom . |

Primary Examiner—James B. Marbert
Attorney, Agent, or Firm—Richard R. Trexler

[57] ABSTRACT

The present invention provides a combined tweezers and magnifier instrument wherein the parts may be snap-connected for ease of assembly, sterility, cleanliness and facility of use.

4 Claims, 1 Drawing Sheet

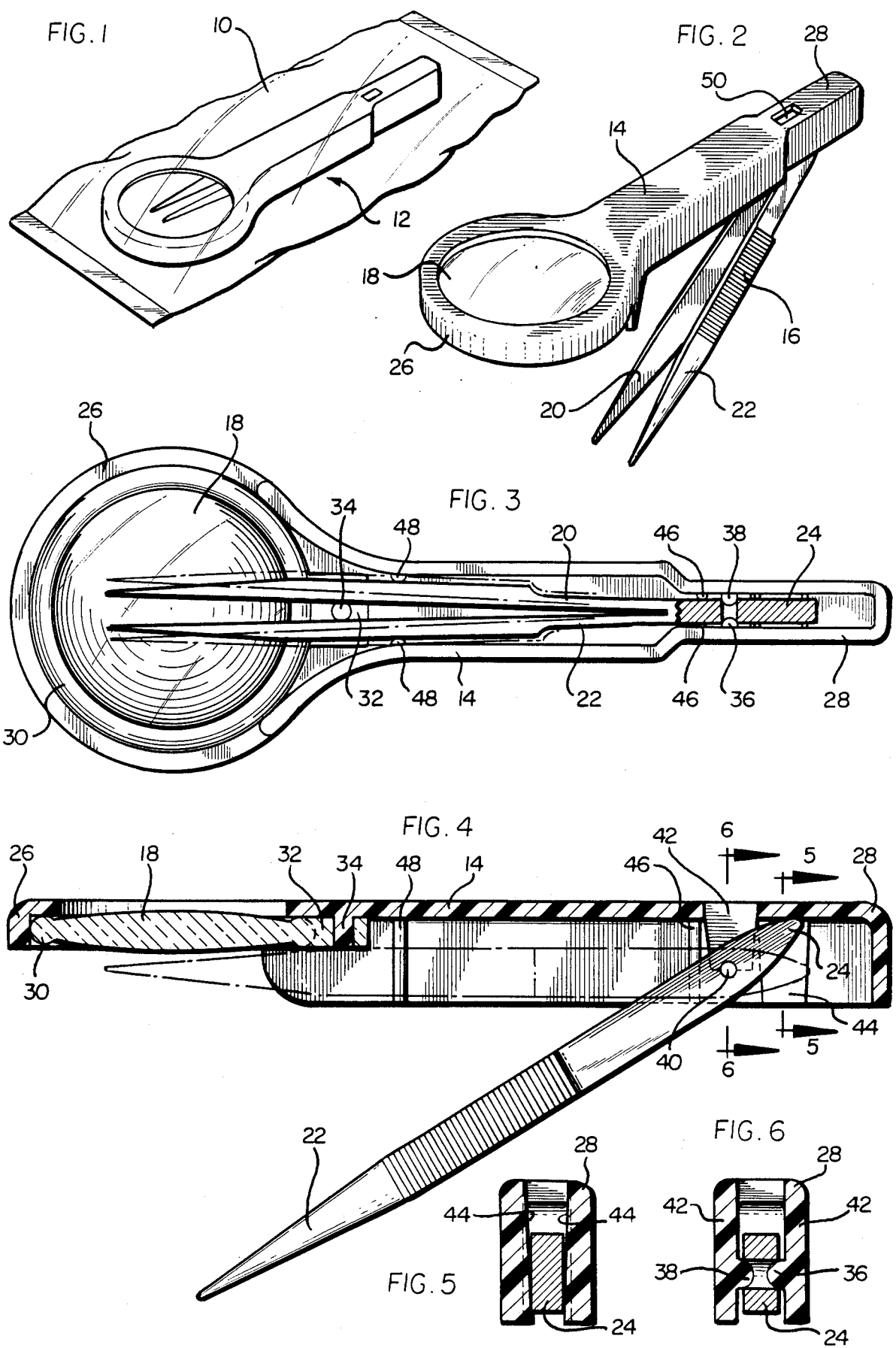

TWEEZERS AND MAGNIFIER

This application is a continuation of application Ser. No. 038,738, filed Apr. 15, 1987, now abandoned.

This invention relates to dermatological instruments, and more particularly to instruments providing a combined tweezers and magnifier.

GENERAL STATEMENT

Combined tweezers and magnifiers have been heretofore provided. The present invention provides such an instrument of simplified yet improved construction.

Where tweezers with magnification are to be used, it is desirable that an instrument be provided which is simple in form and readily operable. When used in delicate operations, as for example by doctors or in hospitals, it is desirable that an instrument be provided which may be readily sterilized, and packaged and presented for use in a sterilized manner. It is further desirable that it be so constructed so that it will remain clean, yet readily operable.

It is further desirable that it be constructed to be low in cost so that it may, if necessary, be discarded or replaced in whole or in part, without undue expense.

OBJECTS OF THE PRESENT INVENTION

An important object of the present invention is to provide a combined tweezers and magnifier instrument which may be easily used and also readily sterilized and presented for use in a sterile manner.

A further object of the present invention is to provide a combined tweezers and magnifier instrument fabricated of a minimum number of parts, to facilitate construction and use, as well as to provide simplification.

A further object of the invention is to provide a combined tweezers and magnifier instrument which is durable and readily operable, yet of low cost, so that it may be replaced in whole or in part without undue expense.

Various other objects, advantages and features of the invention will be apparent from the following specification and drawings, wherein a preferred embodiment is set for for purpose of illustration.

BRIEF DESCRIPTION OF THE DRAWINGS

In the drawings, wherein like reference numerals refer to like parts throughout;

FIG. 1 is a perspective view of a tweezers and magnifier combination in association or in assembled condition, within a sterile envelope, and constructed in accordance with a preferred embodiment of the present invention;

FIG. 2 is a perspective view, on an enlarged scale, of the instrument depicted in FIG. 1, assembled, and in open condition, for use;

FIG. 3 is a bottom view of the instrument of FIG. 2, on a further enlarged scale, with selected parts being shown in section;

FIG. 4 is a side view of the structure of FIG. 3, partly in elevation, and partly in section;

FIG. 5 is a sectional view of the structure along the line 5—5 of FIG. 4; and

FIG. 6 is a sectional view of the structure of FIG. 4 along the line 6—6 thereof.

DETAILED DESCRIPTION OF THE ILLUSTRATED EMBODIMENT

Referring further to the drawings, in FIG. 1 there is shown a partial perspective view of a sterile envelope 10 housing a tweezers and magnifier instrument of the invention, generally indicated by the reference numeral 12. Normally the instrument is preassembled, and may be sterilized within the envelope.

More specifically, as shown in FIG. 2, the instrument comprises a housing 14 and tweezers 16, pivotally connected to the housing at one end of the instrument. The housing 14, at its opposite end, carries a magnifier or magnifying glass, as indicated at 18.

The tweezers 16 may be of any conventional construction, but conventionally comprises a metal unit formed of a pair of resilient arms 20 and 22, welded to form a unitary construction at their assembled end, as indicated at 24 in FIG. 3. The tweezer arms, at their opposite end, may be formed of any desired configuration in accordance with the nature of the work to be done by the instrument. As will be understood, the tweezers may be conventionally formed of metal, and the tweezer arms of spring resilient construction.

The details of the housing 14, and magnifier 18, are shown in FIGS. 3 and 4. The housing 14 is preferably formed of plastic; and the magnifier lens 18 is also preferably formed of transparent plastic of optical grade, with the lens body 18 being shaped and configured to provide a magnified image of the desired focal length when the instrument is open for use.

More specifically, the plastic housing 14 comprises an elongated body with which the rim portion, as indicated at 26, is integrally formed. The opposite end of the body, as indicated at 28, FIGS. 2 and 3, is suitably configurated with the rest of the housing to provide a handle portion for the instrument.

Referring more specifically to the magnifier, the lens 18 is preferably configured with a circular rim portion 30, which may be press fitted into the rim 26 of the plastic body or housing 14. The rim 30 of the magnifier is formed with an integral extension 32, FIGS. 3 and 4, perforated and press-fitted onto a pin-like projection 34 of the housing body 14. The lens projection 32 and the body pin 34 may be heat staked, or ultrasonically welded to provide an essentially integral construction.

The manner in which the tweezers and body or housing 14 are assembled and mounted together is shown in FIGS. 3-6. As shown in FIG. 3, the housing 14, in the vicinity of the handle portion 28, is provided with a pair of projections 36 and 38 integrally formed with and extending from the opposite sidewalls of the handle. The end portion 24 of the tweezers is provided with a perforation to form companion recesses as indicated in FIG. 6, and at 40 in FIG. 4, to receive the housing projections 36 and 38 in a pivotal or swivel manner. The sidewalls of the housing have sufficient resiliency so that the tweezers may be mounted into assembled position, merely be pressing the tweezers into position, causing the projections 36 and 38 to spread apart to receive the tweezers and then snap toward each other to hold the tweezers in pivotal position, the casing sidewalls being of sufficient strength and rigidity to hold the tweezers firmly and frictionally in position so that the tweezers may be manually manipulated between open and closed positions.

As best shown in FIG. 4, the tip of the welded end portion 24 of the tweezers is so configurated that it abuts the wall of the casing 14 when the tweezers are in open position, FIG. 4, at the proper focal length of the lens 18. As further best shown in FIGS. 4 and 6, the sidewalls of the housing are somewhat thickened, as indicated at 42, in the vicinity of the pivot projections 36 and 38 to impart the desired degree of strength and rigidity to the casing sidewalls in the vicinity of the connection.

To preclude inadvertent side motion of the tweezers in their pivotal movement, the casing sidewalls are provided with projections 44, FIGS. 4 and 5, along which and between which the end portion 24 of the tweezers is adapted to slide, to provide the necessary stability. For the same purpose, the sidewalls of the casing are provided with ribs 46, FIGS. 3 and 4, and with ribs or projections 48, FIGS. 3 and 4, the purpose of which is also to lock or hold the tweezers in closed position in resilient engagement with the housing sidewalls when the tweezers are closed as indicated in dotted lines in FIG. 4.

As best shown in FIG. 2, casing 14 may be provided with a window 50 to facilitate formation of the projections and to facilitate proper functioning of the tweezers in pivotal engagement with the casing pivot projections 36 and 38.

Particular attention is directed to the manner in which the tweezers and the plastic magnifier casing 14 may be interconnected, comprising the frictional swivel connection between the casing projections 36 and 38, FIG. 6, and the recesses 40 of the tweezers. As heretofore pointed out, the connection may be made merely by pressing the end portion 24 of the tweezers into proper position. This not only facilitates assembly, but it also facilitates and adapts the instrument for sterilization.

Thus sterilization may be carried out before the parts are assembled, by sterilization or cleaning procedures best adapted for metal, as in the case of the tweezers; and for plastic, in the case of the casing 14 and the magnifier 18. After sterilization and cleaning, the parts may be assembled with a minimum of handling, and if desired, in the operating room of a hospital under insured sterile conditions.

Packaging may be effected in sterile containers, such as indicated at 10 in FIG. 1, with the tweezers and casing assembled, or not yet assembled, but in associated position.

By reason of the snap interconnection between the tweezers and the magnifier housing, as previously described, the tweezers may be removed from the magnifier casing merely by forcefully pulling upon the tweezers to remove the tweezers from the casing projections 36 and 38. By this means various tweezers, having different desired operating end portions may be substituted, using the same magnifier, which may be of considerable cost advantage if the magnifier is fabricated with expensive optical precision. Conversely, different magnifiers may be used with the same tweezers. Removability may be eliminated by configurating the projections 36 and 38 with a cylindrical rather than a spherical configuration.

The entire instrument comprises essentially two pieces, metal in the case of the tweezers, and plastic in the case of the housing 14 with its permanently attached magnifier. The instrument may be manipulated by one hand in its various uses, whether sterile or nonsterile in character.

The invention is hereby claimed as follows:

1. A combined tweezers and magnifier instrument comprising a plastic casing forming a handle for the instrument and having a top closing wall with a holding ring at the front end thereof and depending side walls at least along the opposite rear end thereof; a magnifier lens mounted in said holding ring; tweezers with the free ends of resilient arms disposed selectively beneath said magnifier lens and with the opposite rear ends thereof joined as an integral rear end structure pivotally mounted between the adjacent side walls of the casing and spaced forwardly of the terminal end of the rear end structure of the tweezers; and paired inwardly projecting surfaces on opposite side walls of the casing and disposed adjacently fore and aft of the pivotal mounting of the tweezers for frictional engagement with the integral rear end structure of the tweezers for preventing inadvertent bodily side motion of the tweezers during operation.

2. A combined tweezers and magnifier instrument as claimed in claim 1, wherein the side walls of the casing extend toward the holding ring and are provided with additional inwardly projecting surfaces to frictionally engage the resilient arms of the tweezers in closed position thereof.

3. A combined tweezers and magnifier instrument as claimed in claim 1, wherein the top wall of the casing is provided with a depending pin adjacent the holding ring and interfitted with a recessed projection from the lens.

4. A combined tweezers and magnifier instrument as claimed in claim 1, wherein the side walls of the casing are of limited resiliency and include inward pivot projections, and wherein the rear end structure of the tweezers is provided with aperture means receiving said pivot projections as a snap fitting pivotal mounting for the tweezers facilitating assembly and disassembly thereof.

* * * * *